ASH TREE
Filed Aug. 11, 1971
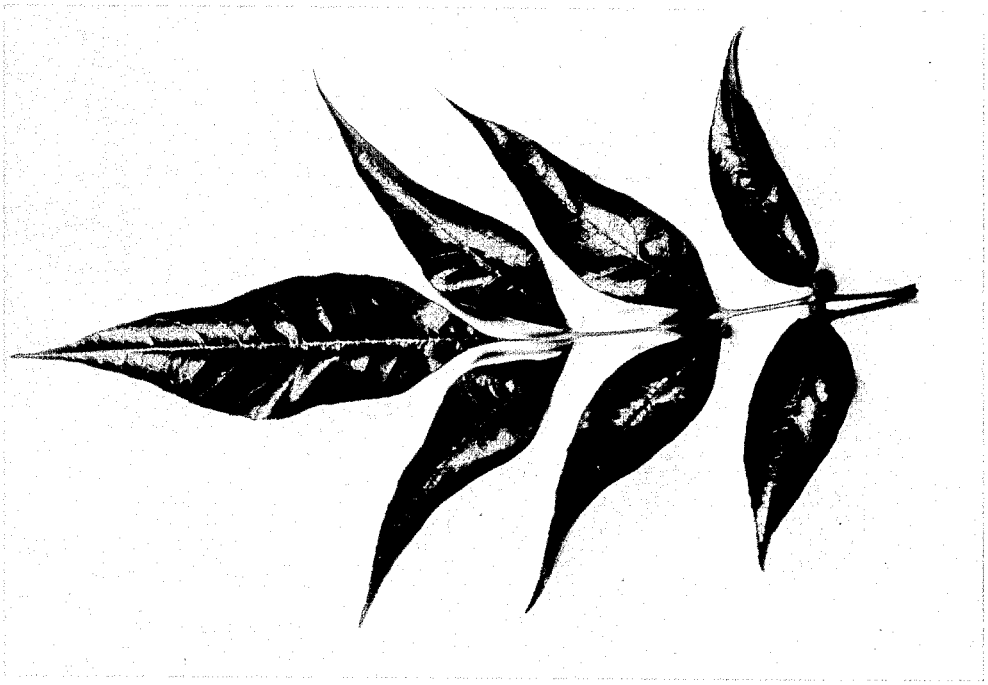
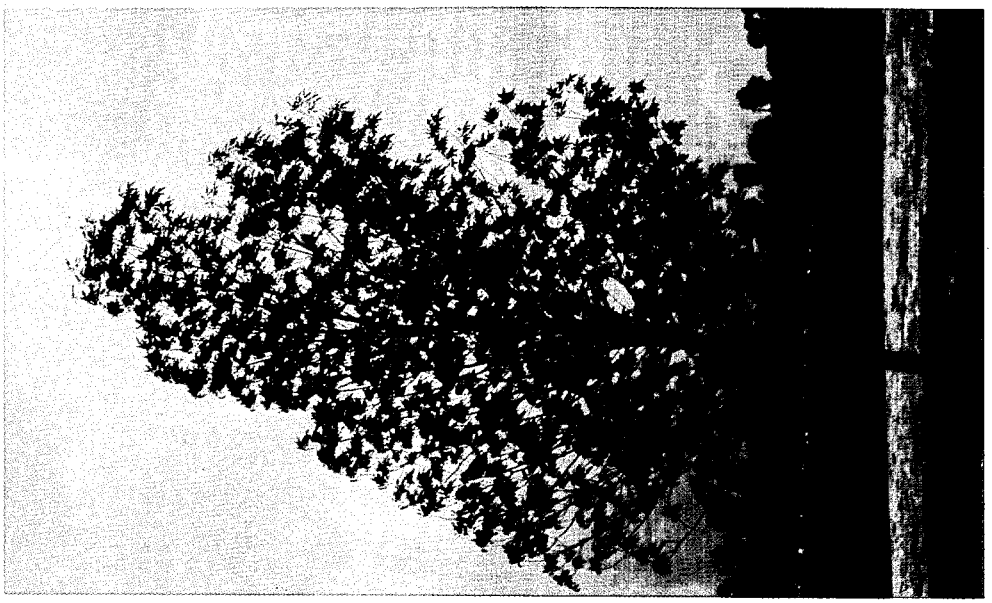
Inventors.
Carl H. Klehm
Roy J. Klehm
By: Robb & Robb
Attorneys.

United States Patent Office

Plant Pat. 3,385
Patented Aug. 21, 1973

3,385
ASH TREE

Carl H. Klehm and Roy G. Klehm, Arlington Heights, Ill., assignors to Klehm Properties, Inc., Arlington Heights, Ill.

Filed Aug. 11, 1971, Ser. No. 170,935
Int. Cl. A01h *5/12*
U.S. Cl. Plt.—51 1 Claim

The present invention relates to a new and distinct variety of ash tree which was discovered by us in our cultivated nursery located at Arlington Heights, Ill., as a newly found seedling of an unnamed and unpatented variety of the species botanically known as *Fraxinus pennsylvanica lanceolata.*

At the time of our discovery aforesaid, we were commercially growing many green ash seedlings in our nursery. In a row of these seedlings which ranged about 5 to 6 feet tall, our attention was attracted to one particular seedling which bore exceptionally shiny leaves. This particular seedling was carefully preserved and kept under close observation. Continued observations and tests thereof for a prolonged period of years have convinced us that this seedling is a new and improved variety, as evidenced by the following unique combination of characteristics which are outstanding therein and which distinguish it from *Fraxinus pennsylvanica lanceolata* as well as from all other varieties of ash trees of which we are aware:

(1) A rapid, vigorous, uniform and seedless habit of growth which requires no staking and only limited pruning;

(2) A wide angle crotching habit of the lateral branches, combined with a strong terminal leader;

(3) Distinctive, narrow, lanceolate leaflets, which present a lacy appearance;

(4) An extremely waxy and shiny leaf cuticle which is thick and scorch resistant; and (5) Good winter hardiness as observed at Barrington and Arlington Heights, Ill.

Asexual reproduction of our new variety as performed by us by budding at Arlington Heights and Barrington, Ill. and also on our behalf at Gresham, Oreg., shows that the foregoing characteristics and distinctions come true to form and are established and transmitted through succeeding propagations.

The acompanying drawing shows a typical tree specimen of our new variety, and also shows typical foliage specimens on a larger scale, as depicted in color as nearly true as it is reasonably possible to make the same in a color illustration of this character.

The following is a detailed description of our new ash tree variety, with color terminology in accordance with the Horticultural Colour Chart, published by the Royal Horticultural Society, of London, England, except where general color terms of ordinary dictionary significance are obvious:

Parentage: A seedling of an unnamed variety of the species botanically known as *Fraxinus pennsylvancia lanceolata.*

Propagation: Holds its distinguishing characteristics through succeeding propagations by budding.

Locality where grown and observed: Arlington Heights and Barrington, Ill. and Gresham, Oreg.

Tree: Large; upright; tall (from 60 to 70 feet); hardy, as indicated by the ability to withstand fall transplanting of bare-root or balled-and-burlaped trees, and the ability to withstand severe desiccating winters such as prevail in northern Illinois and which are sometimes accompanied by lack of snow cover on the ground surface; growth rate of main leader and major upright branches averages from 3 to 4 feet annually, and of minor interior and horizontal branches from 18 to 30 inches, which latter are somewhat faster growing than other varieties such as "Marshall's Seedless Ash" (unpatented); tree shape presents a "haystack" appearance when mature and is similar to that of mature sugar maples.

*Trunk.*—Smooth.

*Branches.*—Smooth. Color—medium gray.

*Lenticles.*—Many.

*Leaves.*—Compound of 5, 7 or 9 leaflets; from 6 inches to 10 inches long.

*Leaflets.*—Length—lateral leaflets from about 4¼ to 4¾ inches long, and terminal leaflet from about 5 to 6 inches long. Width—from 1 to 1⅛ inches. Shape—narow; ovate; pointed; lanceolate. Color—upper surface—Winchester Green, Color No. 131 B (106), with a high degree of gloss. Reverse—dull gray green, with no pubescence, but with pronounced veins. Autumn color—becomes medium yellow similar to autumn color of Norway maple leaves. Margin—mostly smooth edge, but sometimes portions of margins become slightly crinkled and present a lacy appearance. Petiole—from about 1⅛ to 2 inches long. Glands—none. Stipules—none.

Leaf buds:

*Shape.*—Pointed; about ⅛ to 3/16 inch in diameter.

*Color.*—Dusty brown or dark chocolate.

Leaf scar:—Half-moon shaped, with a slight concave depression on the dorsal edge.

Flowers:

*Quantity.*—Abundant.

*Size.*—Small.

*Form.*—Flowers comprise small tufts of lobed apettalous blossoms which appear from 7 to 9 days before leaves are apparent.

*Color.*—Dusty brown.

Seeds: None, as determined from observations of from about 800 to 900 mature trees over a period of about 14 years.

General observations: As compared with the variety known as "Marshall's Seedless Ash" (unpatented) our new variety is a much straighter grower and has a wider crotching habit, with the limbs extending nearly horizontally from the main trunk, while its leaflets are very narrow, substantially smooth edged and are a shiny bright green color, as distinguished from the typical broad, dull, dark green leaflets of the "Marshall's Seedless Ash." Also, the leaflets of our new variety are longer and more pointed in shape, and stay green and hang onto the tree longer than those of "Marshall's Seedless Ash" and common green ash varieties.

We claim:

1. A new and distinct variety of ash tree, substantially as hereinshown and described, characterized particularly as to novelty by the unique combination of a rapid, vigorous, uniform and seedless habit of growth which requires no staking and only limited pruning, a wide angle crotching habit of the lateral branches, combined with a strong terminal leader, distinctive, narrow, lanceolate leaves which present a lacy appearance, an extremely waxy and shiny leaf cuticle which is thick and scorch resistant, and good winter hardiness as observed at Barrington and Arlington Heights, Ill.

References Cited

Cole's Spring Trade List 1962, Cole Nay, Co., Painesville, Ohio, pp. 11–12 relied on.

ROBERT E. BAGWILL, Primary Examiner